(12) United States Patent
Kolanko et al.

(10) Patent No.: US 6,387,618 B1
(45) Date of Patent: May 14, 2002

(54) MICRONUCLEUS ASSAY WITH GENOMIC DNA HYBRIDIZATION PROBE AND ENZYMATIC COLOR PIGMENT DETECTION

(75) Inventors: Christopher J. Kolanko, Derwood; Mark D. Pyle, Laurel, both of MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/272,734

(22) Filed: Mar. 3, 1999

(51) Int. Cl.[7] ............ C12Q 1/68; G01N 33/53; C02H 21/04
(52) U.S. Cl. ............ 435/6; 435/7.5; 435/7.9; 435/7.95; 435/18; 435/28; 436/501; 536/23.1; 536/24.3
(58) Field of Search ............ 435/6, 7.5, 810, 435/18, 28, 7.9, 7.95; 536/23.1, 24.3; 436/501

(56) References Cited

U.S. PATENT DOCUMENTS

| | | | |
|---|---|---|---|
| 4,789,630 A | 12/1988 | Bloch et al. | 435/7 |
| 4,888,272 A | 12/1989 | Singer et al. | 435/6 |
| 4,888,278 A | * 12/1989 | Singer et al. | 435/6 |
| 5,229,265 A | 7/1993 | Tometsko | 435/6 |
| 5,665,549 A | * 9/1997 | Pinkel et al. | 435/6 |

OTHER PUBLICATIONS

Anamthawat–Johsson et al. Discrimination between closely related TRITICEAE species using genomic DNS as a probe. Theor. Appl. Genet. vol. 79, pp. 721–728, Dec. 1990.*

Pierce Chemical Company, 94–95 Pierce Catalog and Handbook, Rockville, IL 1994, pp. T–209 to T–230.

* cited by examiner

Primary Examiner—Stephanie W. Zitomer
(74) Attorney, Agent, or Firm—John J. Karasek; Philip E. Ketner

(57) ABSTRACT

A method for detecting the presence of micronuclei in cells of an organism comprises the steps of (a) isolating cells of the organism, (b) exposing the cells to a hybridization probe, the hybridization probe comprising digested, labeled whole genomic DNA, the digested genomic DNA being labeled with a first binding member capable of specifically binding with a second binding member, whereby, as a result of exposing the cells to the hybridization probe, the hybridization probe binds hybridizes with DNA in the cells, including DNA contained in micronuclei, if present, (c) exposing the cells to a compound comprising the second binding member coupled to an enzyme capable of reacting with a chromogenic substrate to convert the chromogenic substrate into a colored pigment, whereby, as a result of exposing the cells to the compound, the compound binds to the hybridization probe that is hybridized with the DNA in the cells, (d) exposing the cells to the chromogenic substrate, whereby the chromogenic substrate is converted into a colored pigment in the presence of the enzyme, and (e) examining the cells and scoring the cells for the presence or absence of micronuclei.

17 Claims, No Drawings

MICRONUCLEUS ASSAY WITH GENOMIC DNA HYBRIDIZATION PROBE AND ENZYMATIC COLOR PIGMENT DETECTION

BACKGROUND OF THE INVENTION

1. Field of the Invention

The invention relates generally to an assay method and composition for determining genetic toxicity. More particularly, the invention relates to a whole genomic DNA probe and to a method for using the DNA probe in a micronucleus assay.

2. Description of the Related Art

The mouse bone marrow micronucleus assay is used for the detection of damage to chromosomes or mitotic apparatus induced by particular compounds such as pharmaceutical drugs, environmental chemical agents, etc. (see, for example, Schmid, W. "The Micronucleus Test", Mutation Res. 31, 9 (1975 ), Salamone, et al.,"Towards an Improved Micronucleus Test: Studies on 3 Model Agents, Mitomycin C, Cyclophosphamide and Dimethylbenzanthracene:" Mutation Res. 74, 347 (1980), and Heddle, J. A., et al. "The Induction of Micronuclei as a Measure of Genotoxicity: A Report of the U.S. Environment Protection Agency Gene-Tox Program, Mutation Res. 123, 61 (1983), Salamone, M. F. all incorporated herein by reference). The test is based on the observation that mitotic cells with chromatid breaks or chromatid exchanges exhibit disturbances in the anaphase distribution of their chromatin. After telophase, this displaced chromatin can be excluded from the nuclei of the daughter cells and is found in the cytoplasm as a micronucleus.

In the conventional mouse bone marrow micronucleus assay, mice are exposed to a particular test substance, and then bone marrow cells of the exposed animals are isolated. The isolated cells are immediately smeared onto a slide, stained with a reagent and examined under a microscope for the presence of micronuclei. Giemsa stain has traditionally been used as the staining reagent; however, because of the tendency of Giemsa stain to stain artifacts that resemble micronuclei, DNA-specific fluorescent stains such as acridine orange are now being used. See, for example, Hayashi, M., Sofuni, T. and Ishidate, M. Jr. 1983, "An application of acridine orange fluorescent staining to the micronucleus test". Mutat. Research, 120:241–247; Hayashi, M., Morita, T., Kodama, Y., Sofuni, T. and Ishidate, M. Jr. 1990, "The micronucleus assay with mouse peripheral blood reticulocytes using acridine orange-coated slides" Mutat. Research, 245:245–249 and MacGregor, J. T., Wehr, C. M. and Langlois, R. G. 1983, "A simple fluorescent staining procedure for micronucleus and RNA in erythrocytes using Hoechst 33258 and pyronin Y" Mutat. Research, 120:269–275, all incorporated herein by reference.

DNA-specific fluorescent stains used in the mouse bone marrow micronucleus assay have several disadvantages that limit their usefulness. First, fluorescent microscopy requires expensive, specialized fluorescent microscopes equipped with special multi-filter cube switching and low light level video hardware. Fluorescent microscopes require a high degree of technical sophistication to use effectively. Second, fluorescent-stained slides fade over time and therefore cannot be stored and archived for future reference. Third, color signatures achieved by fluorescent detection may be unstable due to differential fluorescent bleaching rates. Fourth, automation of the finding and scoring of fluorescent stained micronuclei is costly and difficult. Finally, fluorescent preparations may cause swelling of chromosomes and loss of fine detail.

Thus, there is a need for a method for detecting micronuclei that allows the use of standard light field microscopy equipment and does not require expensive, specialized fluorescent microscopy equipment. Moreover, there is a need for a method of detecting micronuclei that provides a permanent record of the assay that can be stored and archived. Moreover, there is a need for a method of detecting micronuclei that produces a stable color signature. Moreover, there is a need for a method of detecting micronuclei wherein the finding and scoring of micronuclei can be easily automated. Moreover, there is a need for a method of detecting micronuclei that does not cause the swelling of chromosomes.

SUMMARY OF THE INVENTION

It has now been found that micronuclei in cells may be detected by means of a whole genomic DNA probe coupled with immunoenzymatic color pigment detection.

In particular, the invention provides a method for detecting the presence of micronuclei in cells of an organism. According to the method of the invention, cells of an organism are isolated and exposed to a hybridization probe of digested labeled, whole genomic DNA. The hybridization probe is labeled with a first binding member that allows it to bind specifically to a second binding member. The hybridization probe hybridizes with DNA in the cells, including DNA contained in micronuclei, if present. The hybridization probe is detected by exposing the cells to a compound comprising the second binding member coupled to an enzyme capable of reacting with a chromogenic substrate to convert the chromogenic substrate into a colored pigment. The compound binds to the first binding member. When the cells are exposed to a chromogenic substrate, the chromogenic substrate is converted into a colored pigment, thereby indicating the presence and location of DNA in the cells. The presence of micronuclei is indicated by the presence of colored pigment outside the nucleus of the cells. The cells are then examined and scored for the presence or absence of micronuclei.

In another aspect, the invention provides a hybridization probe for detecting micronuclei in mouse cells, the hybridization probe being made by digesting whole genomic mouse DNA into DNA fragments and then labeling the DNA fragments.

In another aspect, the invention provides a test kit for assaying cells for the presence of micronuclei, the test kit comprising (a) a hybridization probe, the hybridization probe comprising digested, labeled whole genomic DNA, the digested genomic DNA being labeled with a first binding member capable of specifically binding with a second binding member, (b) a compound comprising the second binding member coupled to an enzyme capable of reacting with a chromogenic substrate to convert the chromogenic substrate into a colored pigment, and (c) a chromogenic substrate.

The invention overcomes the above-described disadvantages of the conventional fluorescent staining in a micronucleus assay. The use of a DNA-specific whole genomic DNA hybridization probe minimizes the staining of cell artifacts and thereby minimizes false positive results in the micronucleus assay. The colored pigment used in the detection of micronuclei can be visualized using standard light field microscopy, and expensive specialized fluorescent microscopes is not needed. Brightfield illumination may be used instead of epi-illumination (which is required to excite flurescence preparations and which is more uneven). The colored pigment used in the invention allows for permanent staining of cells, which allows for assay slides to be stored, archived and reanalyzed for years. The color signatures used in color pigment detection according to the present invention are more stable than fluorescent preparations and there is less variation in intensity of labeled elements within fields of view and between fields. The automation of finding and scoring of micronuclei is more easily achieved. The method of hybridization and color pigment staining of the present invention is less likely to cause swelling of chromosomes and loss of fine detail than methods of fluorescent staining.

DESCRIPTION OF THE PREFERRED EMBODIMENTS

Micronuclei may form in cells of an animal that is exposed to a genetically toxic substance or environment. The micronucleus assay, which involves exposing an animal to a particular substance or environment, then isolating cells from the animal and examining them for the presence of micronuclei, is a method for screening drugs and chemical agents to determine their genetic toxicity. See, for example, U.S. Pat. No. 5,229,265 to Tomesko; Parton, J. W., Probst, G. S. and Garriot, M. L. 1988, "The in vivo effect of 2,6-xylidine on induction of micronuclei in mouse bone marrow cells", Mutat Research 206:281–283; Parton, J. W., Garriott, M. L. and Beyers, J. E. 1991, "Expulsion of demecolcine induced micronuclei from mouse bone marrow polychromatic erythrocytes", Environ. and Molecular Mutagenesis 17:79–83; Styles, J. A., Richardson, C. R. and Burlinson, B. 1983, "A comparison of the incidence of micronuclei in blood and bone marrow in three strains of mouse dosed with cyclophosphamide or hexamethylphosphamide (HMPA)" Mutat Research, 122:143–147, all incorporated herein by reference.

Tomesko, U.S. Pat. No. 5,229,265, at page 1, lines 31–56, states that blood cells provide a sensitive model for evaluating clastogenic events since the nucleus of the erythrocyte stem cell is expelled a few hours after the last mitosis yielding DNA deficient cells. Treatment with clastogens or spindle positions which cause chromosomal breaks in the stem cells result in the formation of easily detectable micronuclei (MNs) in these anucleated young polychromatic erythrocytes (PCEs). These young anucleated cells are still rich in RNA and, therefore, exhibit unique staining patterns that distinguishes them from the mature normochromatic erythrocytes (RBCs). For example, when blood is stained with a metachromatic dye such as acridine orange (AO), . . . the DNA of a micronucleus exhibits a bright green-yellow fluorescence. In contrast the young RNA rich anucleated PCEs exhibit red fluorescence when stained with AO and excited with a 488 nm light source. The RNA rich polychromatic cells (PCEs) find their way into the blood stream and eventually complete their evolution to the RNA deficient and nonfluorescent normochromatic red blood cells—the mature RBCs. The brief existence of the PCE cells (about 48 hours) has been used by practitioners of the art to define the time frame for the conventional micronucleus assay by counting only MN in the PCE population.

The formation of a micronucleus in a cell exposed to a genetically toxic agent is the result of breakage of a chromatid or chromosome or the result of lagging of one or more whole chromosomes at anaphase. Because the event is random, that is, because there is no way to predict in advance which portion of which chromosome will break or lag to form a micronucleus, the present invention uses whole genomic DNA as a hybridization probe to detect DNA outside the nucleus of the cell! Before use as a hybridization probe, the whole genomic DNA is digested and labeled.

Whole genomic DNA may be obtained by any known means of isolating whole genomic DNA. See, for example, Sambrook, J., Fritsch, E. F. and Maniatis, T. 1989, Molecular Cloning, A Laboratory Manual, $2^{nd}$ Edition, Cold Springs Harbor Laboratory Press, Colds Spring Harbor, N.Y. For many species, whole genomic DNA is commercially available. For example, human, rat and mouse genomic DNA is available from Promega, Madison, Wis.

So that the whole genomic DNA can move about cells easily and hybridize with any fragment of DNA that may be contained in a micronucleus, the whole genomic DNA is digested with a restriction enzyme before it is used as a hybridization probe. Preferably, the whole genomic DNA is digested with DNase I for a sufficient time to cut the genomic DNA into fragments of about 100 base pairs (bp) to about 1000 base pairs.

An additional aspect of the present invention is the use of enzyme-linked labels that produce an insoluble precipitate for the detection of the fragments of the whole genomic DNA in cells. To enable the use of enzyme-linked labels, the digested fragments of the whole genomic DNA are labeled with a functional group that is capable of binding to a binding partner that is linked to the enzyme. For example, the fragments of DNA may be labeled with biotin and the enzyme may be linked to avidin or strepavidin, which have a strong binding affinity to biotin. The labeling of the DNA fragments may be accomplished by any method known in the art, including, for example, nick translation to incorporate labeled nucleotides into the fragments of DNA.

In the method of the present invention, cells of an organism are isolated, preferably by spreading onto microscope slides. The cells are exposed to the labeled, digested whole genomic DNA so that the whole genomic DNA fragments hybridize to cellular DNA, including the DNA of micronuclei, if present. Methods known in the art for hybridizing DNA probes to cellular DNA may be used. See, for example, Haar, F-M, Markus D., Michael H., Horst L. and Cremer, C. 1996, "Optimization of Fast-FISH for alpha-satellite DNA Probes" J Biochem. Biophys. Methods 33:43–54., incorporated herein by reference. The cells are then exposed to the enzyme, which is coupled to a functional group that causes the enzyme to bind to the whole genomic DNA fragments. The cells are then exposed to a chromogenic substrate of the enzyme, which creates an insoluble color pigment precipitate that identifies the location of the whole genomic DNA fragments. Micronuclei, if present in the cells, may be detected by examining the cells for the presence of color pigment outside of the nucleus. A counterstain such as Wright's Giesma stain may be added to aid in the differentiation of cell types and in the identification of micronuclei. Preferably, the examination of the cells for the presence of micronuclei is done by brightfield microscopy. The step of scoring the cells may be accomplished by any means of making note of cells that contain micronuclei. The cells may then be scored according to the presence or absence of micronuclei. The method of the present invention, particularly the process of examining and scoring the cells may be automated and computer controlled. The slides may then be archived for future reference.

Any binding partners, enzymes and substrates known in the art for enzymatic labeling and detection and for creating permanent stains may be used in the present invention. Preferably, the enzyme is a peroxidase, such as horse radish peroxidase, or alkaline phosphatase. Chromogenic substrates for horse radish peroxidase include 3,3',5,5' tetramethylbenzidine (TMB), 3,3'-diaminobenzidine (DAB), and 3-amino-9-ethyl carbazol (AEC). Chromogenic substrates for alkaline phosphatase include BCIP/NBT, Fast Red and AP-Orange. Avidin-linked enzymes and chromogenic substrates are commercially available from, for example, Pierce Chemical Company (Rockville, Ill.) and Sigma (St. Louis, Mo.). Enzymatic labeling and detection are described, for example, in U.S. Pat. No. 4,789,630 to Bloch et al and in Pierce Chemical Company, 94–95 Pierce Catalog and Handbook, Rockville, Ill. 1994, pages T-209 to T-230, both incorporated herein by reference.

The following table provides typical enzyme-substrate pairs that can be used in the method of the present invention:

TABLE 1

Enzyme linked immunostaining detection of either horseradish peroxidase (HRP) or alkaline phosphatase (Alk Phase).

| ENZYME LABEL | SUBSTRATE | BRIGHTFIELD COLOR |
| --- | --- | --- |
| HRP | 3,3-Diaminobenzidine (DAB) | Brown |
| HRP | Aminoethylcarbozole (AEC) | Red |
| HRP | Tetramethylbenzidine (TMB) | Green |
| Alk Phase | BCIP/NBT | Purple |
| Alk Phase | Fast Red TR | Red |
| Alk Phase | AP-Orange | Orange |

An advantage of using color pigment staining is that, unlike fluorescent-stained slides which fade after a few weeks, color pigment-stained slides are permanent and may be archived for future reference.

Having described the invention, the following examples are given to illustrate specific applications of the invention including the best mode now known to perform the invention. These specific examples are not intended to limit the scope of the invention described in this application.

EXAMPLE 1

Preparation of bone marrow slides from the excised femurs of cyclophosphamide-treated mice and evaluation of micronucleated polychromatic erythrocytes were conducted as described by Parton, J. W., Probst, G. S. and Garriot, M. L. 1988, "The in vivo effect of 2,6-xylidine on induction of micronuclei in mouse bone marrow cells" Mutat Research 206:281–283, incorporated herein by reference. The iliac end of the excised femurs was removed and a 00 sable hair brush, wetted with fetal bovine serum (Gibco, Grand Island, N.Y.), was inserted into the marrow canal and rotated back and forth. The sample was streaked onto a microscope slide. The procedure was repeated until four streaks were made from the femur, according to the procedure described in Styles, J. A., Richardson, C. R. and Burlinson, B. 1983, "A comparison of the incidence of micronuclei in blood and bone marrow in three strains of mouse dosed with Cyclophosphamide or hexamethylphosphamide (HMPA)" Mutat Research, 122:143–147, incorporated herein by reference.

The mouse micronucleus probe was synthesized by taking whole mouse genomic DNA (Promega, Madison Wis.) and extensively digesting with 0.0005 units/$\mu$l DNase I (Sigma, St Louis, Mo.) at 37° C. for 10 minutes followed by DNase inactivation at 70° C. for 10 minutes. (At this point the digested DNA can be stored at −20° C. indefinitely.) One $\mu$gram of the digested mouse genomic DNA was nick translated in a reaction mixture containing 5.0 $\mu$l of 0.53 mM biotin-14-dUTP (Boehringer Mannheim, Indianapolis, Ind.), 1.0 $\mu$l of 10 U/$\mu$l Polymerase I (Sigma), 10 $\mu$l solution of 0.2 mM dNTP's (dTTP, dGTP, dCTP (Boehringer Mannheim) in a solution of 500 mM Tris (pH 8.0), 50 mM $MgCl_2$, 100 mM 2-mercaptoethanol, 100 $\mu$g bovine serum albumin) in a total volume of 100 $\mu$l (Sambrook et al., 1989). The reaction was incubated at 15° C. for 2 hours and stopped with 6 $\mu$l of 500 mM EDTA. Biotin-labeled DNA was separated from unincorporated nucleotides with a Sephadex G-50 spin column. The labeled-probe was hybridized by the Fast-hybridization procedure, following the procedure described in Haar, F-M, Markus D., Michael H., Horst L. and Cremer, C. 1996, "Optimization of Fast-FISH for alpha-satellite DNA Probes", J Biochem. Biophys. Methods 33:43–54, to mouse bone marrow slides previously fixed in 100% methanol for 30 minutes and then allowed to air dry for 20 minutes. The mouse genomic probe (0.10 $\mu$g) was added to the Fast-hybridization buffer mixture (3 $\mu$l working hybridization buffer (100 mmol Tris-HCl; 30 mmol $MgCl_2$; 500 mmol KCl; 10 mg gelatin; pH 8.3 at 20° C.) plus 3 $\mu$l 20×SSC (saline sodium citrate) and 24 $\mu$l distilled $H_2O$ total volume of buffer is 30 $\mu$l) and applied to the mouse bone marrow spreads. The slide was coversliped, all air bubbles were removed, and the edges of the coverslip were sealed with rubber cement. Each slide was incubate for 5 minutes at 70° C. on a heating block to denature both cellular and probe DNA and then immediately placed on a second heating block pre-equilibrated to 37 C° for 55 minutes. After Fast-hybridization the coverslip was removed and the slides were quickly placed in a solution of 1×PBS/0.2% Tween-20 for 5 minutes at room temperature and then blocked in a solution of 1% non-fat dry milk in sterile filtered 1×PBS at 37 C° for 1 hour. Just prior to immunostaining probe detection slides were washed in 1×PBS for 5 minutes and then followed by the addition of 200 $\mu$l of avidin-horse radish peroxidase (Avidin-HRP) (Sigma) diluted in sterile filtered 1×PBS (1:10,000 dilution). Each slide was coversliped and incubated in a humidity chamber at 37° C. for 1 hour. After incubation the slides were washed in 1×PBS, 3× for 5 minutes at room temperature (slides can be stored in 1×PBS at 4°C. before development) followed by immunoenzymatic probe detection with the compound aminoethylcarbazole (AEC) (Sigma) to form a red precipitate.

A stock solution of 0.4 grams of AEC was dissolved in 100 mls of dimethyl formamide (Sigma) and stored at 4° C. (stock solution can be stored for 2 months). Prior to probe detection 1 ml of AEC stock was added to 15 ml of 0.1 M sodium acetate (pH 5.2) and 15 $\mu$l of 30% hydrogen peroxide. The AEC solution was filtered through a Whatman No. 1 filter and 100 $\mu$l was applied directly to the slide and allowed to incubate for 10 minutes. AEC color detected slides were then washed for 5 minutes in 1×PBS and then counterstained with either 4% Giemsa in phosphate buffer or by the Wright's Giemsa staining technique according to Parton et al. 1988. The reaction of the HRP with AEC and peroxide formed a dark red precipitate that aided in detection of both the cellular DNA and micronuclei found within the PCE and NCE cells. When counterstained with Wright's Giemsa, a dark red coloration of the DNA by the probe is observed in both the micronuclei and in the intracellular DNA.

EXAMPLE 2

The procedures of Example 1 were repeated, except that 3'3-Diaminobenzidine (DAB) was used instead of AEC.

0.025 grams of 3'3-diaminobenzidine was dissolved in 40 ml of 0.05 M Tris buffer (pH 7.6) and 8.3 µl of 30% hydrogen peroxide followed by filtering through a Whatman No. 1 filter paper. Each slide was immersed in DAB solution for 5 minutes and the reaction stopped by placing the slides in 1×PBS for 5 minutes followed by counterstaining. The DAB formed a a brown to black precipitate.

Obviously, many modifications and variations of the present invention are possible in light of the above teachings. It is therefore to be understood that, within the scope of the appended claims, the invention may be practiced otherwise than as specifically described.

What is claimed is:

1. A method for detecting the presence or absence of micronuclei in anucleated young polychromatic erythrocytes (PCEs) and normochromatic erythrocytes (NCEs) of an organism in a sample, comprising
    (a) isolating PCEs and NCEs of the organism,
    (b) exposing the PCEs and NCEs to a hybridization probe, the hybridization probe comprising digested, labeled whole genomic DNA, the digested genomic DNA being labeled with a first binding member capable of specifically binding with a second binding member,
    whereby, as a result of exposing the PCEs and NCEs to the hybridization probe, the hybridization probe hybridizes with DNA contained in PCEs and NCEs as micronuclei, if present,
    (c) exposing the PCEs and NCEs to a compound comprising the second binding member coupled to an enzyme capable of reacting with a chromogenic substrate
    whereby, as a result of exposing the PCEs and NCEs to the compound, the compound binds to the hybridization probe that is hybridized with the DNA in the PCEs and NCEs as micronuclei, if present,
    (d) exposing the PCEs and NCEs to the chromogenic substrate, whereby the chromogenic substrate is converted into a colored pigment by reaction with the enzyme,
    (e) examining the PCEs and NCEs for the presence of colored pigment, the presence of colored pigment indicating the presence of micronuclei in the PCEs and NCEs, and
    (f) scoring the sample according to the presence or absence of micronuclei in the PCEs and NCEs.

2. The method of claim 1 before (e), further comprising exposing the PCEs and NCEs to a counter-stain.

3. The method of claim 1 wherein the whole genomic DNA is from the same species as the organism.

4. The method of claim 1 wherein the sample comprises rodent bone marrow cells.

5. The method of claim 1 wherein the sample comprises mouse bone marrow cells.

6. The method of claim 1 wherein the first binding member is biotin and the second binding member is avidin or streptavidin.

7. The method of claim 1 wherein the enzyme is a peroxidase and the chromogenic substrate is selected from the group consisting of 3,3',5,5' tetramethylbenzidine (TMB), 3,3'-diaminobenzidine (DAB), and 3-amino-9-ethyl carbazol (AEC).

8. The method of claim 7 wherein the peroxidase is horseradish peroxidase.

9. The method of claim 1 wherein the enzyme is alkaline phosphatase and the chromogenic substrate is selected from the group consisting of BCIP/NBT, Fast Red and AP-Orange.

10. The method of claim 1 wherein examining the PCEs and NCEs is carried out by brightfield microscopy.

11. The method of claim 1 further comprising archiving the sample for a period of at least two weeks.

12. A method for detecting the presence or absence of micronuclei in rodent bone marrow cells, comprising
    isolating the rodent bone marrow cells,
    exposing the rodent bone marrow cells to a hybridization probe, the hybridization probe comprising digested, labeled whole genomic DNA, the digested genomic DNA being labeled with a first binding member capable of specifically binding with a second binding member,
    whereby, as a result of exposing the rodent bone marrow cells to the hybridization probe, the hybridization probe hybridizes with a DNA fragment as micronuclei, if present,
    exposing the rodent bone marrow cells to a compound comprising the second binding member coupled to an enzyme capable of reacting with a chromogenic substrate
    whereby, as a result of exposing the rodent bone marrow cells to the compound, the compound binds to the hybridization probe that is hybridized with the DNA fragment as micronuclei, if present,
    exposing the rodent bone marrow cells to the chromogenic substrate, whereby the chromogenic substrate is converted into a colored pigment by reaction with the enzyme,
    examining the rodent bone marrow cells for the presence of colored pigment, the presence of colored pigment indicating the presence of micronuclei in the rodent bone marrow cells, and
    scoring the rodent bone marrow cells according to the presence or absence of micronuclei in the rodent bone marrow cells.

13. The method of claim 12 wherein the whole genomic DNA is from the same species as the rodent bone marrow cells.

14. The method of claim 12 wherein the first binding member is biotin and the second binding member is avidin or streptavidin.

15. The method of claim 12 wherein the enzyme is a peroxidase and the chromogenic substrate is selected from the group consisting of 3,3',5,5' tetramethylbenzidine (TMB), 3,3'-diaminobenzidine (DAB), and 3-amino-9-ethyl carbazol (AEC).

16. The method of claim 15 wherein the peroxidase is horseradish peroxidase.

17. The method of claim 12 wherein the enzyme is alkaline phosphatase and the chromogenic substrate is selected from the group consisting of BCIP/NBT, Fast Red and AP-Orange.

* * * * *